(12) United States Patent
Rehbein

(10) Patent No.: US 11,285,268 B2
(45) Date of Patent: Mar. 29, 2022

(54) MEDICAMENT DELIVERY DEVICE

(71) Applicant: SANOFI-AVENTIS DEUTSCHLAND GMBH, Frankfurt am Main (DE)

(72) Inventor: Christian Rehbein, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 113 days.

(21) Appl. No.: 16/068,027

(22) PCT Filed: Jan. 5, 2017

(86) PCT No.: PCT/EP2017/050222
§ 371 (c)(1),
(2) Date: Jul. 3, 2018

(87) PCT Pub. No.: WO2017/118705
PCT Pub. Date: Jul. 13, 2017

(65) Prior Publication Data
US 2019/0217016 A1   Jul. 18, 2019

(30) Foreign Application Priority Data
Jan. 6, 2016   (EP) ..................... 16150290

(51) Int. Cl.
*A61M 5/178*   (2006.01)
*A61M 5/315*   (2006.01)
(Continued)

(52) U.S. Cl.
CPC .......... *A61M 5/31553* (2013.01); *A61M 5/20* (2013.01); *A61M 5/2033* (2013.01);
(Continued)

(58) Field of Classification Search
CPC .......... A61M 5/31553; A61M 5/31551; A61M 2005/3125; A61M 2005/3126; A61M 2205/3306; A61M 2205/3327
See application file for complete search history.

(56) References Cited

U.S. PATENT DOCUMENTS

2006/0224123 A1 * 10/2006 Friedli .............. A61M 5/31525
                                                                        604/207
2009/0318865 A1   12/2009 Moller et al.
(Continued)

FOREIGN PATENT DOCUMENTS

CN   102202711   9/2011
CN   102686257   9/2012
(Continued)

OTHER PUBLICATIONS

International Preliminary Report on Patentability in Application No. PCT/EP2017/050222, dated Jul. 10, 2018, 8 pages.
(Continued)

*Primary Examiner* — Rebecca E Eisenberg
*Assistant Examiner* — Tania Ismail
(74) *Attorney, Agent, or Firm* — Fish & Richardson P.C.

(57) ABSTRACT

A drug delivery device comprises a housing and a dose sleeve located within the housing, the dose sleeve being configured to move helically within the housing as a medicament dose is dialled into or delivered from the drug delivery device. A dose setting arrangement is coupled to the dose sleeve and is configured to cause helical movement of the dose sleeve as a medicament dose is dialled into the drug delivery device through rotation of a dose dial forming part of the dose setting component. A dose delivery arrangement comprising a dose button is coupled to the dose sleeve and is configured to cause delivery of medicament with helical movement of the dose sleeve and without rotation of the dose dial when the dose button is actuated. A first sensor
(Continued)

arrangement is configured for detecting a rotation of the dose dial relative to the housing. A second sensor arrangement is configured for detecting movement of the dose sleeve relative to the housing. A processor arrangement is coupled to receive inputs from the first and second sensor arrangements and is configured to calculate therefrom the size of a medicament dose dispensed by the drug delivery device.

20 Claims, 8 Drawing Sheets

(51) Int. Cl.
*A61M 5/20* (2006.01)
*A61M 5/24* (2006.01)
*A61M 5/31* (2006.01)

(52) U.S. Cl.
CPC ........... *A61M 5/24* (2013.01); *A61M 5/31551* (2013.01); *A61M 5/31583* (2013.01); *A61M 2005/202* (2013.01); *A61M 2005/3125* (2013.01); *A61M 2005/3126* (2013.01); *A61M 2205/3306* (2013.01); *A61M 2205/3317* (2013.01); *A61M 2205/3327* (2013.01); *A61M 2205/3561* (2013.01); *A61M 2205/50* (2013.01); *A61M 2205/502* (2013.01)

(56) References Cited

U.S. PATENT DOCUMENTS

| | | | | |
|---|---|---|---|---|
| 2014/0074041 | A1* | 3/2014 | Pedersen | A61M 5/31541 604/211 |
| 2015/0290396 | A1* | 10/2015 | Nagar | G16H 20/13 340/540 |
| 2015/0343152 | A1* | 12/2015 | Butler | A61M 5/31551 604/207 |

FOREIGN PATENT DOCUMENTS

| | | |
|---|---|---|
| CN | 103458945 | 12/2013 |
| CN | 103717246 | 4/2014 |
| CN | 104203315 | 12/2014 |
| CN | 104703641 | 6/2015 |
| CN | 104797282 | 7/2015 |
| CN | 104853788 | 8/2015 |
| CN | 204563169 | 8/2015 |
| CN | 104902944 | 9/2015 |
| CN | 104902945 | 9/2015 |
| CN | 104918649 | 9/2015 |
| CN | 105120925 | 12/2015 |
| CN | 105188812 | 12/2015 |
| JP | H11-267206 | 10/1999 |
| JP | 2015-529492 | 10/2015 |
| WO | WO 02/053214 | 7/2002 |
| WO | WO 2010/052275 | 5/2010 |
| WO | WO 2012/140097 | 10/2012 |
| WO | WO 2012/160159 | 11/2012 |
| WO | WO 2013/120777 | 8/2013 |
| WO | WO 2013/120778 | 8/2013 |
| WO | WO 2014/111340 | 7/2014 |
| WO | WO 2014/111342 | 7/2014 |
| WO | WO 2014/161953 | 10/2014 |
| WO | WO 2014/180744 | 11/2014 |

OTHER PUBLICATIONS

International Search Report and Written Opinion in Application No. PCT/EP2017/050222, dated Apr. 11, 2017, 11 pages.

* cited by examiner

MEDICAMENT DELIVERY DEVICE

CROSS REFERENCE TO RELATED APPLICATIONS

This application is a U.S. national stage application under 35 USC § 371 of International Patent Application No. PCT/EP2017/050222, filed on Jan. 5, 2017, which claims priority to European Patent Application No. 16150290.1, filed on Jan. 6, 2016, the entire contents of each of which are incorporated herein by reference.

TECHNICAL FIELD

The disclosure generally relates to a medicament delivery device.

BACKGROUND

Chronic diseases generally require administering of medicaments or drugs according to a pre-defined time schedule in order to keep the concentration level of a pharmaceutically active substance on a pre-defined level. Many medicaments require administration by way of injection by making use of syringes or syringe-like drug delivery devices. Such devices should be universally applicable and should be operable even by persons without formal medical training.

Moreover, such devices, like pen-type injectors should provide accurate, precise and reliable setting of a dose and subsequent dispensing of the respective medicament. Typically, the medicament to be dispensed and injected is provided in a disposable or replaceable cartridge, such as a vial, an ampoule or a carpule comprising a slideably disposed piston to become operably engaged with a piston rod or lead screw of a drive mechanism of the drug delivery device. The drive mechanism is adapted to apply thrust to the cartridge's piston in distal direction in order to build-up a respective fluid pressure, which in turn leads to a dispensing of the liquid medicament via a dispensing or distal end of the cartridge being typically in fluid connection with a piercing element like an injection needle.

One type of pen injector device is exemplified by the SoloStar (RTM) device from Sanofi. With these types of pen injector, a number sleeve rotates helically as a dose is dialled into the device.

The helical rotation causes a dose selector dial and a dose button that are mounted on the number sleeve to extend axially in a proximal direction from the device, causing the overall length of the pen injector to increase. To deliver a dose, the user presses the dose button and forces the number sleeve back into the housing of the pen injector. WO 2013/120777 discloses a supplemental device that is configured for attachment to such an injector pen. The supplemental device couples to the injector pen and determines dose dialled and delivered by performing optical character recognition on images of a number shown on the number sleeve as the injection pen is operated.

Another type of pen injector device does not have axial movement of a dose selector and dose button as a dose is dialled into the device. Instead, the dose button is connected to a drive shaft and is not directly connected to the number sleeve. During dose dialling and delivery, the number sleeve moves helically within the housing but the dose selector remains at the same axial position. The dose button remains at a fixed axial position during dose dialling.

SUMMARY

According to a first aspect, there is provided a drug delivery device comprising: a housing and a dose sleeve located within the housing. The dose sleeve is configured to move helically within the housing as a medicament dose is dialled into or delivered from the drug delivery device. The drug delivery device includes a dose setting arrangement coupled to the dose sleeve and configured to cause helical movement of the dose sleeve as a medicament dose is dialled into the drug delivery device through rotation of a dose dial forming part of the dose setting component.

The drug delivery device includes a dose delivery arrangement comprising a dose button coupled to the dose sleeve and configured to cause delivery of medicament with helical movement of the dose sleeve and without rotation of the dose dial when the dose button is actuated. The drug delivery device includes a first sensor arrangement for detecting a rotation of the dose dial relative to the housing. The drug delivery device includes a second sensor arrangement for detecting movement of the dose sleeve relative to the housing. The drug delivery device includes a processor arrangement coupled to receive inputs from the first and second sensor arrangements and configured to calculate therefrom the size of a medicament dose dispensed by the drug delivery device.

By providing a first and a second sensor arrangement, both a rotational but also a longitudinal or axial displacement of the at least one dosing arrangement of the drug delivery device relative to the housing can be precisely determined. This way, a dose setting but in particular a dose dispensing procedure executable by the drug delivery device can be detected and recorded in a redundant way. Moreover, by means of a first and second sensor arrangements adapted to detect different types of relative movement between the at least dosing arrangement relative to the housing of the drug delivery device or relative to the fastening member, the medicament delivery device can precisely distinguish between a dose dispensing and a dose setting procedure.

By means of the first and the second sensor arrangement an axial displacement and rotational displacement of one and the same dose setting component of the drug delivery device can be independently measured and quantitatively determined. Besides to provide a certain redundancy the signals provided by the two sensors can be compared to distinguish between different configurations of the drug delivery device, in particular to distinguish between a dose setting and a dose dispensing procedure.

Furthermore, by making use of first and second sensor arrangements, the internal mechanical construction of the medicament delivery device can be simplified, rendering the medicament delivery device particularly robust, reliable, durable and failure-safe.

The medicament delivery device may be a disposable or reusable pen-type injector.

The first sensor arrangement may comprise a first scale attachable to the rotatable dose dial member of the drug delivery device and comprises a first sensor arranged on the sliding member and cooperating with the first scale.

The first sensor may be enabled to visually detect rotation of the dose dial member.

The first sensor may comprise optical transmitting and detecting transducers directed at the dose dial member.

The dose dial member may comprise features and the first sensor may comprise first and second sensor components located such as to detect the features of the dose dial member as the dose dial member rotates. Here, the processor arrangement may be configured to calculate from a phase of signals provided by first and second sensor components the direction of rotation of the dose dial member.

The first scale may comprise an incremental encoder.

The second sensor arrangement may be configured to detect axial movement of the dose sleeve relative to the housing.

The second sensor arrangement may be configured to detect rotational movement of the dose sleeve relative to the housing.

The second sensor arrangement may comprise a second scale and a second sensor cooperating with the scale, wherein the sensor and the corresponding scale are subject to a relative displacement when the dose sleeve moves relative to the housing. The second scale may be provided on a dose sleeve, e.g. a number sleeve. The second scale may comprise tick marks.

The drug delivery device may comprise a display configured to display a currently dialled dose. The processor arrangement may be configured to store data indicative of a delivered dose in non-volatile memory.

The drug delivery device may further comprise a cartridge which is at least partially filled with a medicament.

Advantageously, the first sensor arrangement and/or the second sensor arrangement is adapted to quantitatively determine a rotational and/or axial displacement of the dosing arrangement of the drug delivery device relative to the housing of the drug delivery device and/or relative to the fastening member of the medicament delivery device. At least one of the two sensor arrangements is therefore adapted to determine the size or the path length of a relative axial and/or rotational displacement between the dosing arrangement and the housing of the drug delivery device. Here, the axial displacement and the rotational displacement alone may each be directly indicative of the size of a set dose or of a dispensed dose. Moreover, the size of a dose may also be determined on the basis of a combination of measured axial and rotational displacements.

In particular, the first sensor arrangement is adapted to quantitatively determine a rotational displacement of the dose setting component relative to the housing of the drug delivery device.

The second sensor arrangement in turn is adapted to quantitatively determine an axial displacement of the dose sleeve relative to the housing of the drug delivery device, although axial displacement may be inferred from rotational or helical movement.

Advantageously at least one of first and second sensor arrangements comprises a sensor cooperating with a scale or scale member comprising such a scale. Here, the respective sensor and its corresponding scale are intended to become subject to a relative displacement when the dose sleeve is subject to a movement relative to the housing of the drug delivery device. The sensor may be based on a tactile, optical, magnetic or electrical sensor principle. Hence, the scale may be correspondingly encoded so that detectable signals can be generated by the at least one sensor in response of a relative movement between the scale and its corresponding sensor. Typically, the scale and its corresponding sensor both belong to the respective sensor arrangement or build up the same.

The at least one sensor arrangement may be either adapted to determine absolute or relative positions or orientations between the sensor and its corresponding scale or it may be configured to only determine incremental changes of the relative position or orientation between the sensor and its corresponding scale.

In effect, by means of the first and second sensor arrangements, a dialling in or setting of a dose of medicament can be separately detected and measured in terms of a longitudinal or axial displacement of the dose sleeve and in terms of a rotational displacement of a dose setting arrangement. Apart from providing a redundancy this separate detection of an angular and a translational movement of the dose setting arrangement can be further exploited to increase accuracy of the dose size determination.

Since the rotational movement of a dose dial of the drug delivery device is to be detected by means of the first sensor arrangement, a frictional engagement of the medicament delivery device with a dose dial member of the drug delivery device is generally not required. Consequently, the dose dial member of the drug delivery device is directly accessible to the user, thus enhancing the patient's acceptance to make use of the medicament delivery device.

The scales of either or both of the first and second sensor arrangements may be incrementally encoded in a direction of movement relative to the first and/or second sensor. This way, sensors of the first and/or second sensor arrangements are capable to allow determination of an incremental displacement between first and/or second sensors relative to their corresponding first and/or scales, respectively.

The processor arrangement is adapted to distinguish between a dose setting and a dose dispensing procedure of the drug delivery device on the basis of a comparison of first and second signals obtainable from the first and the second sensor arrangements.

The medicament delivery device is particularly adapted to monitor and to record dose dispensing procedures, in particular the time of dose dispensing procedure as well as the size of the dose dispensed. By precisely distinguishing between a dose setting and a dose dispensing procedure, also a correction of a dose setting prior to execute a dose dispensing procedure can be detected and taken into account.

It will be further apparent to those skilled in the art that various modifications and variations can be made without departing from the spirit and scope of the invention. Further, it is to be noted, that any reference signs used in the appended claims are not to be construed as limiting the scope of the present invention.

BRIEF DESCRIPTION OF THE DRAWINGS

In the following, embodiments will be described by making reference to the drawing, in which.

DETAILED DESCRIPTION

Figure 1:
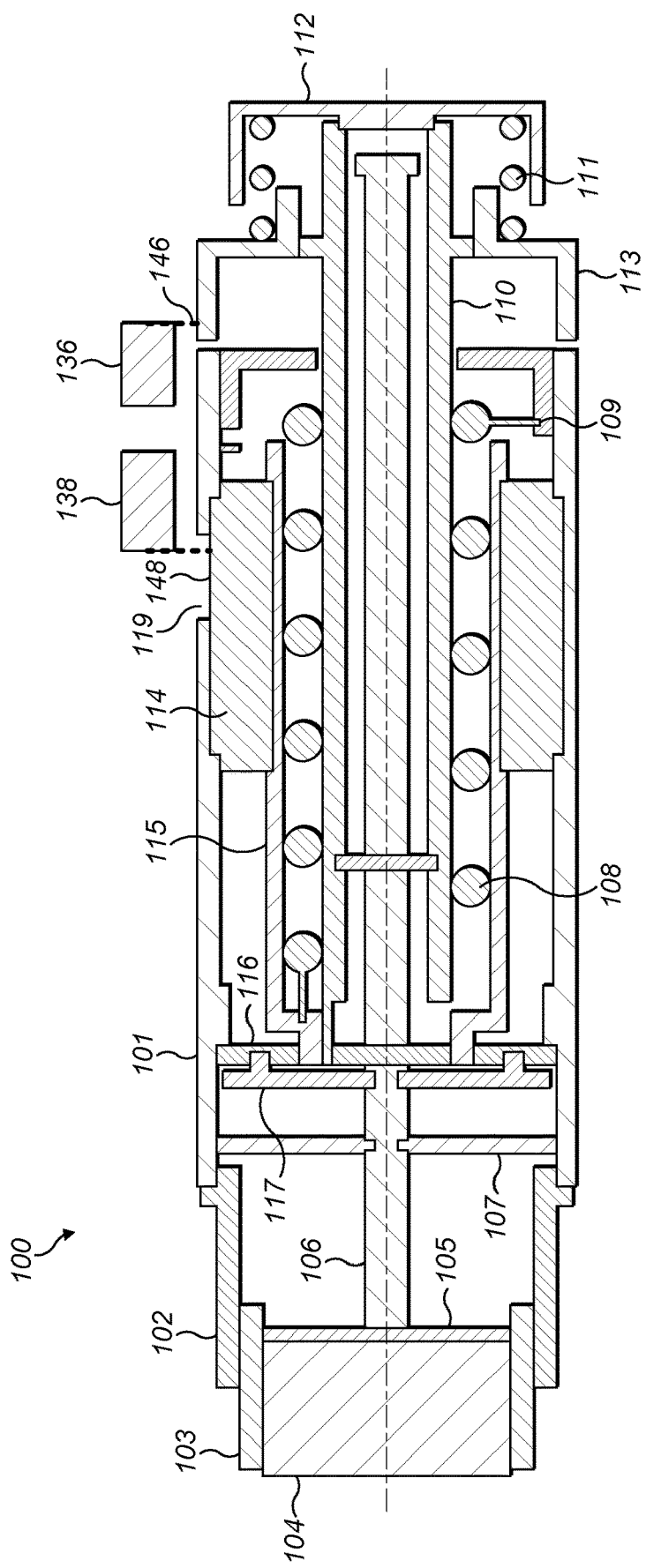
FIG. 1 schematically illustrates a drug delivery device of pen injector type in a cross-section view.

In FIG. 1 a drug or medicament delivery device 100 in form of a pen-type injector in accordance with some embodiments is schematically illustrated. The device 100 is of elongated or substantially tubular shape. It comprises three housing components, a proximal main housing or body 101, a distally located cartridge holder 102 and a releasable protective cap (not shown) to cover the cartridge holder 102 when the drug delivery device 100 is not in use. The cartridge holder 102 is adapted to accommodate and to support a cartridge 103 being at least partially filled with the medicament to be dispensed by means of the drug delivery device 100.

The cartridge 103 typically comprises a vial or carpule having a pierceable seal or septum at its distal end (not shown). The cartridge 103 further comprises a bung 104 at a proximal end to engage with a lead screw of a drive mechanism, which is accommodated and supported in the body 101. By displacing the lead screw 106 in a distal direction (left as shown in the Figure) a well-defined amount of the medicament provided in the cartridge 103 can be dispensed via a needle assembly (not shown). Typically, a double-tipped needle assembly is to be removably screwed on the threaded socket as shown at the distal end of the cartridge holder 102.

For inspecting the filling level of the cartridge 103, which may be of vitreous type, the cartridge holder 102 comprises at least one lateral inspection window (not shown).

In the proximal direction (right in the Figure), the drug delivery device 100 terminates with a dosing arrangement by way of which a user can individually set and subsequently dispense a dose of the medicament. By means of a dose dial member or dose selector 113, a dose of medicament can be dialled into the drug delivery device 100 for delivery to a patient. The dialled dose may be increased by a user rotating the dose selector 113 anticlockwise (counter-clockwise) when viewed looking at the proximal end of the drug delivery device 100.

Once a dose has been set by rotating the dose selector 113, the size of the dose may be corrected at any time by appropriately rotating the dosing selector 113. Rotation in the opposite direction (clockwise in this example) decreases the dialled dose.

Whether or not a dialled dose is adjusted, the extended dosing arrangement 114, 113, 112 may then become subject to a distally directed depression, which is to be conducted and induced by a user by applying a force to the proximally located dose button 112 in the distal direction (left in the figure).

Internal within the drug delivery device 100 are a number of components that cooperate to provide dose dialling and delivery functions. Dose dialling is achieved primarily by the dose selector 113 in cooperation with the dose sleeve 114 and a ratchet sleeve 115. Dose delivery is achieved primarily by the dose button 112 in cooperation with a drive shaft 110, a drive spring 108, the lead screw 106 and the bung 105. A bearing is located between the lead screw 106 and the bung 104. The bearing facilitates rotation of these components relative to one another. The lead screw 106 passes through a thread nut 107 and a spline nut 117 as well as a locking nut 116. A zero stop 109 limits helical movement of the dose sleeve 114 to the zero dose position and prevents movement past that point. The injection devices described in WO002/053214 and US 2009/318865 may be used as the drug delivery device 100 with little or no modification.

Because of action of a clutch (not shown) that is activated when the dose button is pressed, the dose selector 113 does not rotate with the dose sleeve when the dose is being delivered by the drug delivery device 100.

The cartridge holder 102 is a further housing component, and is arranged at a distal end of the proximal housing 101. The cartridge holder 102 has the cartridge 103 arranged therein. The cartridge 103 at least partially filled with a medicament to be injected. Especially with disposable drug delivery devices, a pre-filled cartridge, of vial- or carpule-like type is readily arranged in the drug delivery device.

Figure 9:
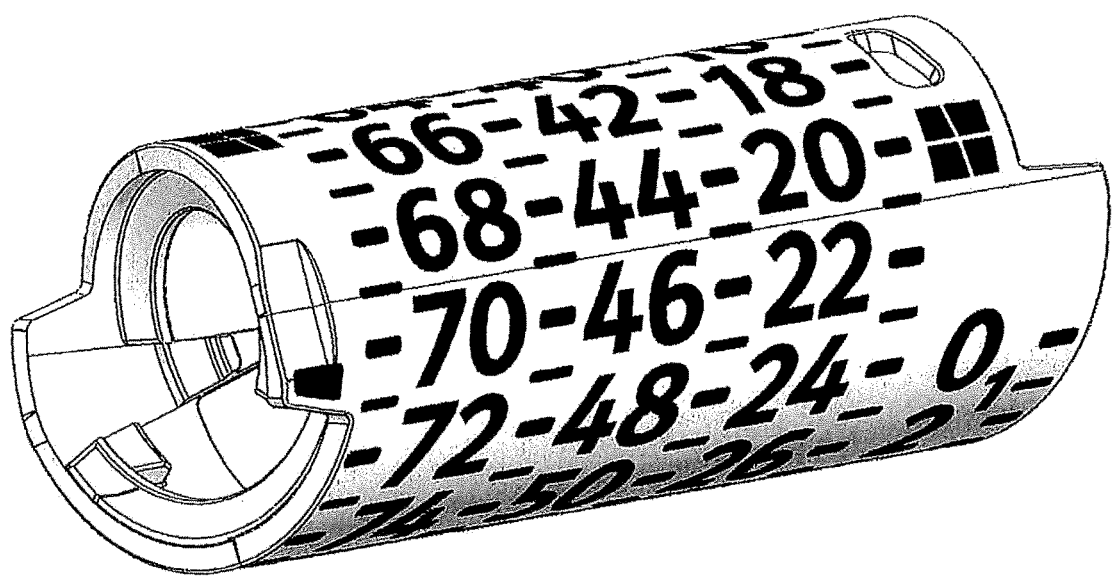
FIG. 9 is an isometric view of a dose sleeve or number sleeve that forms part of the FIG. 1 drug delivery device.

The dose sleeve 114 is a number sleeve. It has a scale of numbers formed thereon in a helical manner. The numbers are accompanied by tick marks. The numbers and tick marks are shown in FIG. 9. The numbers indicate a number of units of dose that is currently dialled into the drug delivery device 100. The currently dialled dose is visible to a user though a dose indication window 119. The dose indication window 119 is located at a proximal portion of the body 101, as illustrated in FIG. 1. By identifying the number that is currently shown in the dose indication window 119, the user can identify the size, in standard units, of the actually set or dialled dose.

When exerting distally directed pressure to the dose button 112 for dispensing of a previously set dose, a dose of medicament is delivered. This involves axial movement of the lead screw 106, causing pressure to be exerted on the bung 104 and thus the expulsion of medicament from the drug delivery device 100.

The drug delivery device 100 further comprises a first sensor arrangement 136, 146 and a second sensor arrangement 138, 148. Each sensor arrangement 136, 146, 138, 148 comprises a sensor 136, 138 and a corresponding scale or other detectable feature 146, 148, by way of which the screw-like (helical) rotation and axial displacement of the dose dialling and delivery arrangement can be separately detected and quantitatively determined. Signals from the sensor arrangements 136, 146, 138, 148 are processed by electronic components of the drug delivery device which are described below with reference to FIG. 7.

The first sensor arrangement comprises a sensor 136 provided on the body 101, and a set of features 146. The set of features are provided on the dose dial member 113 of the drug delivery device 100, In particular on the outer circumference of the dose dial member 113. The type and form of the set of features may depend on the type of sensor 136, which may for instance be implemented as an optical, haptic, electrical or magnetic sensor. The first sensor 136 is enabled to e.g. visually detect a rotation of the dose dial member 113, e.g. on the basis of an optic inspection of its circumferential surface. For instance, the first sensor 136 may comprise optical transmitting and detecting transducers directed at the dose dial member 113, e.g. adapted to evaluate a reflected speckle pattern provided by a comparatively rough surface of the dose dial member 113. Other example arrangements for the first sensor arrangement are shown in FIGS. 2 to 6.

The set of features 146 may constitute an incremental encoder, which is either integrally formed or embedded on or in the dose dial member 113 or which is separately arranged on the circumferential surface.

Due to the fixed axial location of the dose dial member 113, the relative axial locations of the first sensor 136 and the first scale 146 is substantially fixed and remains constant irrespective of the does dialled into the drug delivery device 100. The first sensor arrangement 136, 146 is therefore capable of incrementally detecting any rotational movement of the dose dial member 113 relative to the body 101.

The second sensor arrangement 138, 148 comprises a second sensor 138 and a scale 148. The second sensor 138 is arranged on or in the body 101. The scale 148 is provided on the dose sleeve 119. By way of the second sensor arrangement 138, 148 an axial relative displacement of the dose sleeve 114 in the body 11 can be quantitatively detected.

The scale 148 can be constituted by the tick marks on the number sleeve. This constitutes an incrementally encoded scale 148 allowing to precisely determine the axial path length the dose sleeve 114 moves during dose setting and/or during dose dispensing procedures.

In the case of the scale 148 being an incrementally encoded scale 148, for instance being formed of tick marks, the second sensor is configured to detect the movement of the scale and the direction of movement. Direction of movement can be achieved using two sensing elements at different locations and detecting a phase difference between signals provided by the sensing elements.

Figure 2:
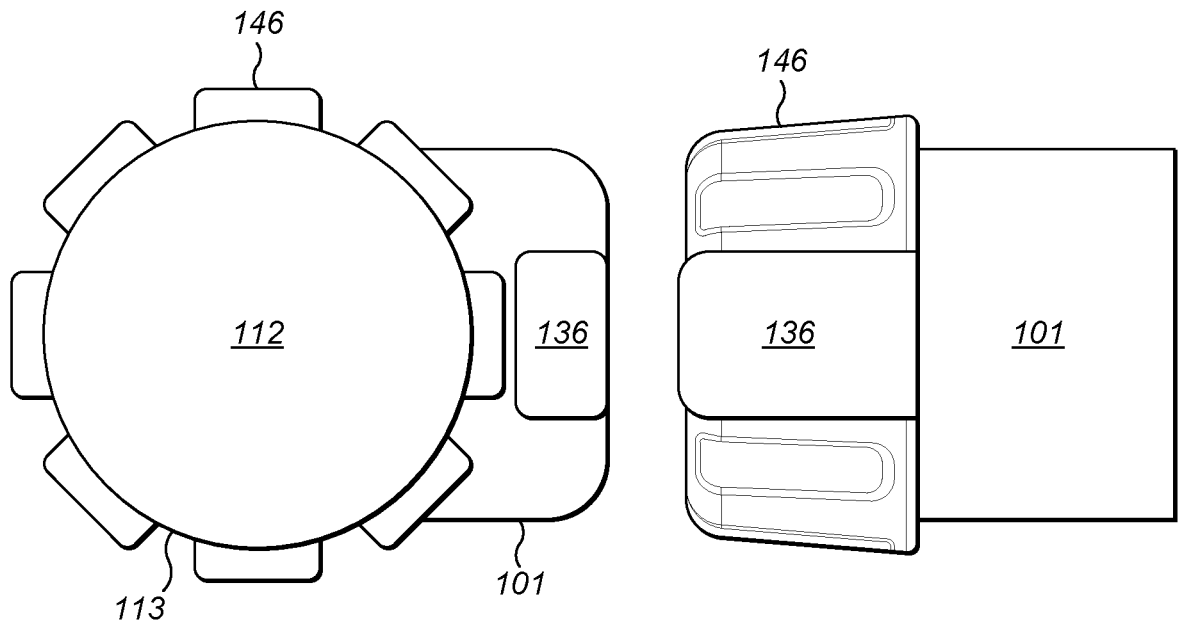
FIG. 2 is an end-on view and a side view of the FIG. 1 drug delivery device with a first form of sensor arrangement.

One form for the first sensing arrangement 136, 146 is shown in FIG. 2. Here, the dose setting dial 113 includes a set of features 146 comprising gnarls, protrusions or ribs on its circumference. The sensor 136 comprises a proximity sensor which is configured to sense the presence and direction of movement of the features past the sensor 136. From the output of the sensor 136, the processor arrangement is able to detect the direction of movement and the distance of movement of the features. The direction of movement is interpreted by the processor arrangement into a clockwise or counter-clockwise direction of movement.

Figure 3:
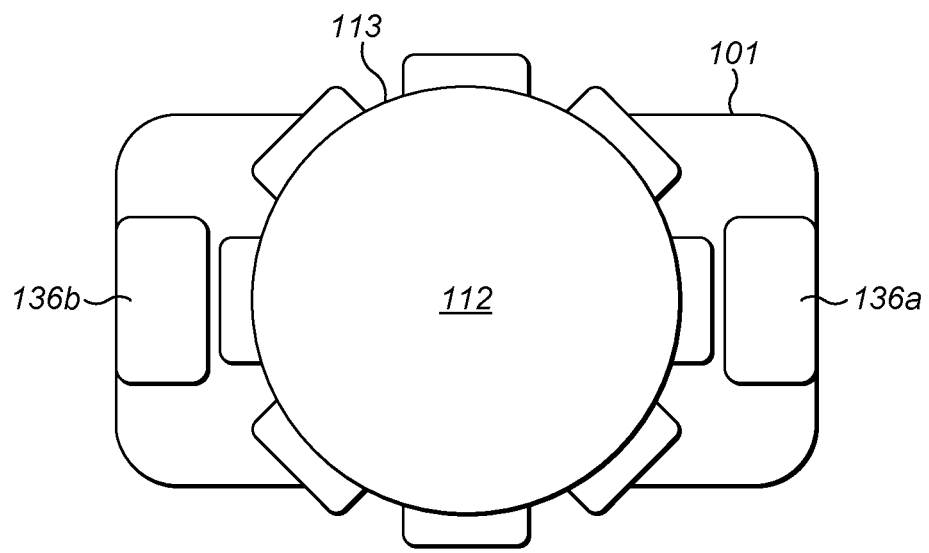
FIG. 3 is an end-on view of the FIG. 1 drug delivery device with a second form of sensor arrangement.
Figure 4A:
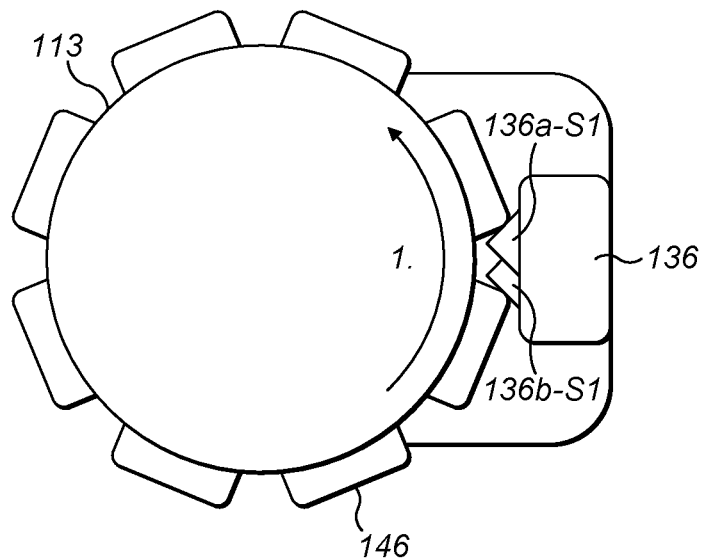
FIGS. 4a, 4b, 4c and 4d are end-on views of the FIG. 1 drug delivery device with a third form of sensor arrangement in different positions of a dose selector.
Figure 4B:
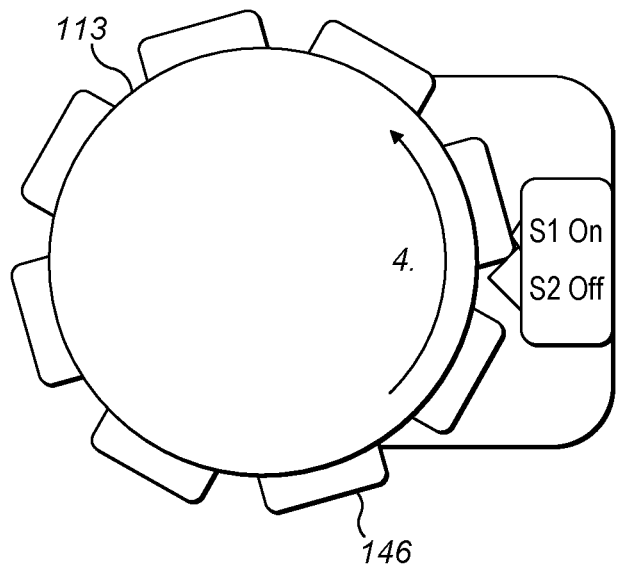
Figure 4C:
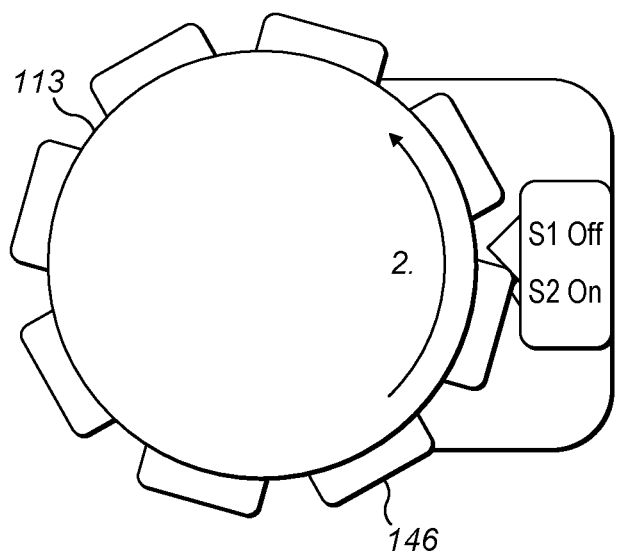
Figure 4D:
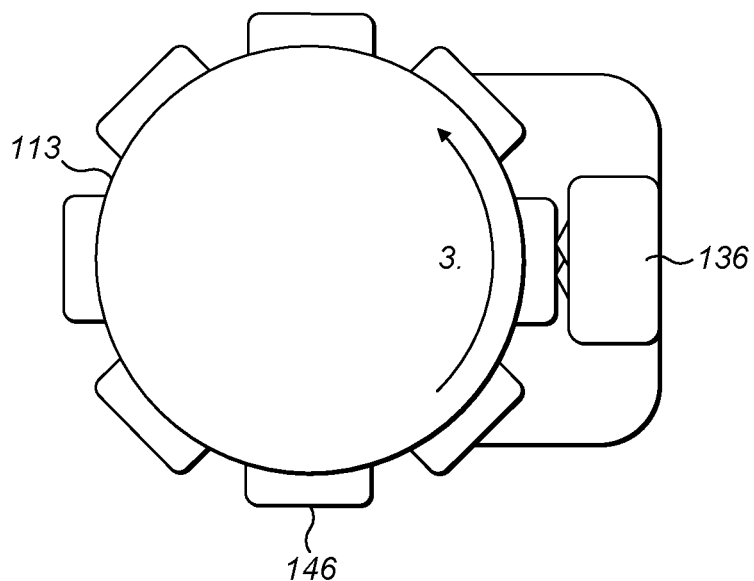

Another form for the first sensing arrangement 136, 146 is shown in FIG. 3. Here, the dose setting dial 113 includes a set of features 146 comprising gnarls, protrusions or ribs on its circumference. The sensor 136 comprises two proximity sensors 136a, 136b, each configured to sense the presence and direction of movement of the features 146. The sensors 136a, 136b are oppositely located, with respect to the dose dial 113. From the output of the sensors 1361, 136b, the processor arrangement is able to detect the direction of movement and the distance of movement of the features. The direction of movement is interpreted by the processor arrangement into a clockwise or counter-clockwise direction of movement. By having the sensors 136a, 136b slightly offset from one another, a phase of signals provided by the sensors 136a, 136b can be detected by the processor arrangement and used to identify or confirm the direction of rotation.

A further form for the first sensing arrangement 136, 146 is shown in FIGS. 4a to 4d. Here, the dose setting dial 113 includes a set of features 146 comprising gnarls, protrusions or ribs on its circumference. The sensor 136 comprises first and second electro-mechanical switches, microswitches, ultra microswitches or subminiature microswitches 136a-S1 and 136b-S2 which are together configured to sense the presence and direction of movement of the features past the sensor 136. The microswitches 136a-S1 and 136b-S2 are located such that they are actuated by the features 146 as the features pass by. The microswitches 136a-S1 and 136b-S2 are located such that first one microswitch, then both, then the other microswitch is activated by the features 146 as the features pass by. The sequence of microswitch activation indicates the direction of movement of the features past the microswitches. From the output of the sensor 136, the processor arrangement is able to detect the direction of movement and the distance of movement of the features. The direction of movement is detected from the phase of signals provided by the microswitches 136a-S1 and 136b-S2. The direction of movement is interpreted by the processor arrangement into a clockwise or counter-clockwise direction of movement. In moving in a counter-clockwise direction, the sequence is FIG. 4a, then 4c then 4d and finally 4b. In moving in a counter-clockwise direction, the sequence is FIG. 4a, then 4b then 4d and finally 4c.

Figure 5:
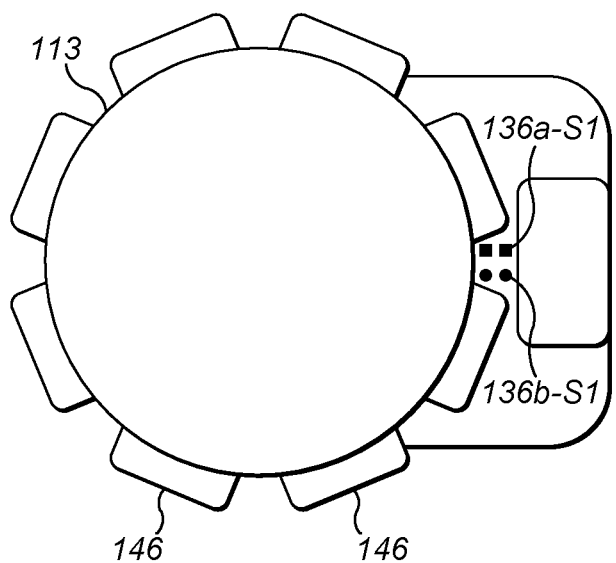
FIG. 5 is an end-on view of the FIG. 1 drug delivery device with a fourth form of sensor arrangement.

A further form for the first sensing arrangement 136, 146 is shown in FIG. 5. Here, the dose setting dial 113 includes a set of features 146 comprising gnarls, protrusions or ribs on its circumference. The sensor 136 comprises first and second optodetectors 136-S1 and 136-S2 which are together configured to sense the presence and direction of movement of the features past the sensor 136. The optodetectors 136a-S1 and 136b-S2 may be photodiodes, light dependent resistors, etc. The optodetectors 136a-S1 and 136b-S2 are located such that they are covered wholly or partially by the features 146 as the features pass by. When covered, the ambient light falling on the optodetectors 136a-S1 and 136b-S2 reduces. This allows the presence of the features at the location of the optodetectors 136a-S1 and 136b-S2 to be detected. The optodetectors 136a-S1 and 136b-S2 are located such that first one optodetector, then both, then the other optodetector is covered by the features 146 as the features pass by. The sequence of optodetectors activation indicates the direction of movement of the features past the optodetectors 136a-S1 and 136b-S2. From the output of the sensor 136, the processor arrangement is able to detect the direction of movement and the distance of movement of the features. The direction of movement is detected from the phase of signals provided by the optodetectors 136a-S1 and 136b-S2. The direction of movement is interpreted by the processor arrangement into a clockwise or counter-clockwise direction of movement.

Figure 6:
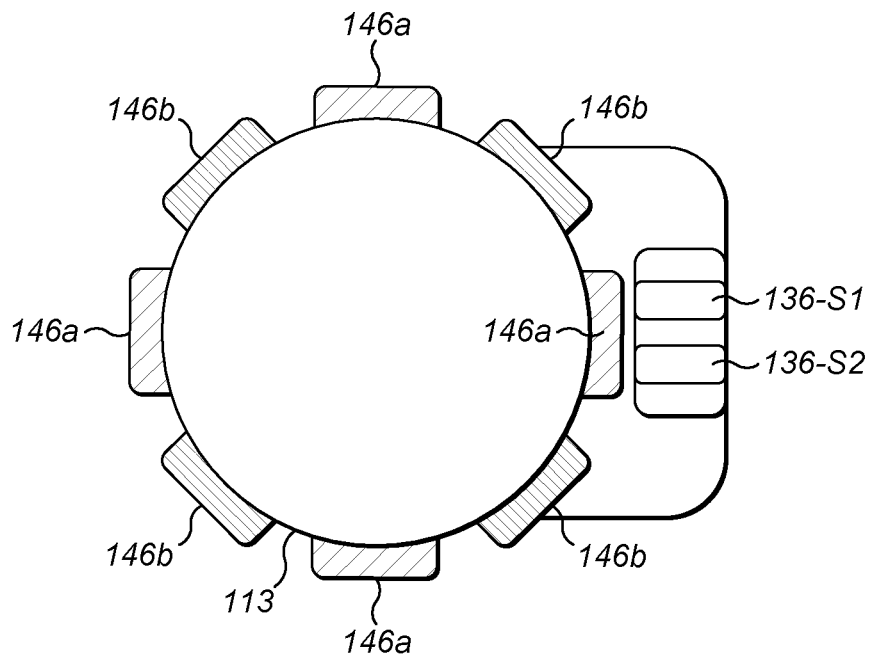
FIG. 6 is an end-on view of the FIG. 1 drug delivery device with a fifth form of sensor arrangement.

A still further form for the first sensing arrangement 136, 146 is shown in FIG. 6. Here, the dose setting dial 113 includes a set of features 146 comprising gnarls, protrusions or ribs on its circumference. The features have a magnetic property, either in that they are magnetic or have magnetic permeability that is very different to air and so affect the earth's magnetic field that is measurable near to the features. The sensor 136 comprises first and second magnetic sensors 136-S1 and 136-S2, such as Hall-effect sensors. The first and second magnetic sensors 136-S1 and 136-S2 are together configured to sense the presence and direction of movement of the features past the sensor 136. The first and second magnetic sensors 136-S1 and 136-S2 are located such that they their output signals change as the features 146 pass by them and the magnetic field experienced at the sensor changes. The sequence of first and second magnetic sensors 136-S1 and 136-S2 field changes indicates the direction of movement of the features past the sensors. From the output of the sensor 136, the processor arrangement is able to detect the direction of movement and the distance of movement of the features. The direction of movement is detected from the phase of signals provided by the first and second magnetic sensors 136-S1 and 136-S2. The direction of movement is interpreted by the processor arrangement into a clockwise or counter-clockwise direction of movement. In moving in a counter-clockwise direction, the sequence is FIG. 4a, then 4c then 4d and finally 4b. In moving in a counter-clockwise direction, the sequence is FIG. 4a, then 4b then 4d and finally 4c.

In all of FIGS. 2 to 6 there are eight features shown as part of the set of features 146, but the greater the number of features then the greater the resolution of measurement that is achievable.

During dose setting and dose dialling, both sensors 136, 138 generate and provide respective first and second signals to a processor arrangement 134.

By continuously comparing the signals obtainable from the first and the second sensors 136, 138 the processing member 34 is able to process said signals may precisely distinguish and recognize the beginning and the end of a dose setting or dialling procedure and the beginning and end of a dose dispensing procedure.

This way, the medicament delivery device 10 can precisely detect, monitor and store such dispensing parameters, which reflect the amount of the medicament which has been actually dispensed by the drug delivery device 100. Moreover, this can be achieved fully automatically, without requiring user acknowledgement or other input.

Figure 7:
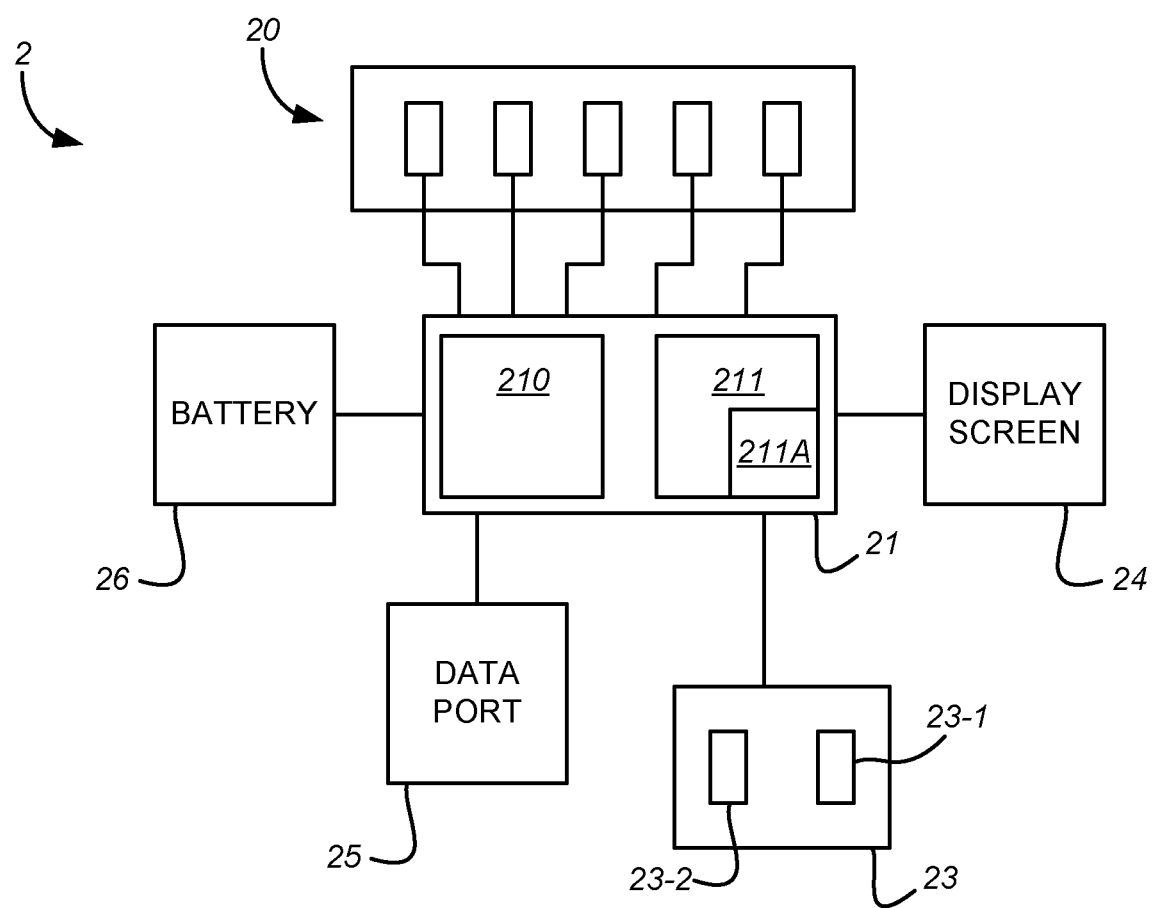
FIG. 7 is a simplified block diagram of electronic components of the FIG. 1 drug delivery device.

FIG. 7 is a simplified schematic block diagram of electronic components of the drug delivery device 100. The sensors 136, 146, 138, 148, which are discussed above, are configured to output signals to the circuitry 21.

The circuitry 21 may be of any suitable composition and may comprise any combination of one or more processors and/or microprocessors 210 (for simplicity, hereafter referred to as "the at least one processor") suitable for causing the functionality described herein to be performed. The circuitry 21 may additionally or alternatively comprise any combination of one or more hardware-only components such as ASICs, FPGAs etc. (which are not shown in FIG. 7).

The circuitry 21 may further comprise any combination of one or more non-transitory computer readable memory media 211, such as one or both of ROM and RAM, which is coupled to the at least one processor 210. The memory 211 may have computer-readable instructions 211A stored thereon. The computer readable instructions 210, when executed by the at least one processor 210 may cause the sensor device 2 to perform the functionality described in this specification, such as controlling operation of the sensors 136, 146, 138, 148 and interpreting the signals received therefrom.

The drug delivery device 100 may further comprise one or both of a display screen 24 (such as an LED or LCD screen) and a data port 25. The display screen 24 may be operable under the control of the circuitry 21 to display information regarding operation of the drug delivery device 1 to the user. For instance, the dialled dose determined by the drug delivery device 100 may be displayed to the user. Other information which can be determined by the drug delivery device 100 includes the drug being dispensed, and/or a history of previously-dispensed doses.

The data port 25 may be used to transfer stored information relating to the operation of the drug delivery device 100 from the memory 211 to a remote device such a PC, tablet computer, or smartphone. Similarly, new software/firmware may be transferred to the sensor device via the data port 25. The data port 25 may be a physical port such as a USB port or may be a virtual, or wireless, port such as an IR, WiFi or Bluetooth transceiver.

The drug delivery device 100 may further comprise a removable or permanent (preferably rechargeable with e.g. photovoltaic cells) battery 26 for powering the other components of the drug delivery device 100. Instead of the battery 26, a photovoltaic or capacitor power source may be used. Other electrical components which are not shown in FIG. 7, but which may nonetheless be included in the drug delivery device 100 include a trigger buffer, a regulator, a voltage suppressor and a charger chip, for charging the rechargeable battery if present.

Figure 8:
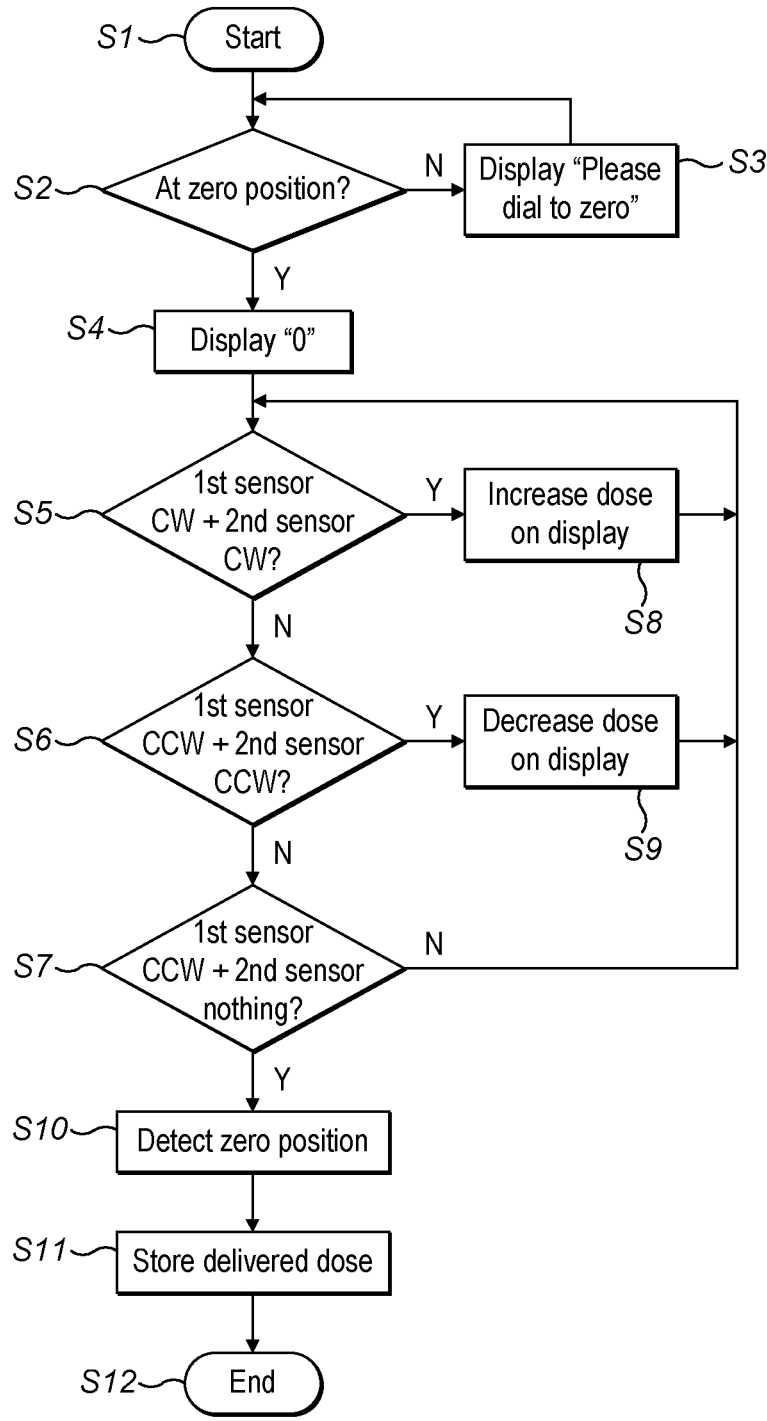
FIG. 8 is a flow chart illustrating operation of a processor arrangement of the FIG. 1 drug delivery device.

Operation will now be described with reference to FIG. 8. FIG. 8 is a flowchart showing operation of the processor arrangement based on inputs from the first and second sensor arrangements 136, 138.

The operation starts at step S1. At step S2, the processor arrangement determines whether the medicament delivery device 100 is at a zero dose position, i.e. that zero dose is dialled into the medicament delivery device 10. On a negative determination, at step S3 the processor arrangement causes display of a message reading: "Please dial to zero" before returning to step 2. Once it is determined that the dose dialled is zero, the operation proceeds to step S4. Here, the processor arrangement causes display of the message: "0", indicating that a zero dose is dialled into the medicament delivery device 10.

At step S5, the processor arrangement determines whether both the first sensor arrangement is indicating a clockwise movement of the dose setting component 113 and the second sensor arrangement is indicating a clockwise rotation of the dose sleeve 114 within the body 101. If not, the operation proceeds to step S6.

At step S6, the processor arrangement determines whether both the first sensor arrangement is indicating a counter-clockwise movement of the dose setting component 113 and the second sensor arrangement is indicating a counter-clockwise rotation of the dose sleeve 114 within the body 101. If not, the operation proceeds to step S7.

At step S7, the processor arrangement determines whether both the first sensor arrangement is indicating a counter-clockwise movement of the dose setting component 113 and the second sensor arrangement is indicating no rotation of the dose sleeve 114 within the body 101. If not, the operation returns to step S5.

If at step S5 the processor arrangement determines that both the first sensor arrangement is indicating a clockwise movement of the dose setting component 113 and the second sensor arrangement is indicating a clockwise rotation of the dose sleeve 114 within the body 101, the operation proceeds to step S8. This occurs because the processor arrangement has detected that a dose that is set or dialled into the medicament delivery device 100 is being increased. At step S8, the value of the displayed dose is increased. The increase is made continuously such that the displayed dose value represents the dose that is set. The amount of the increase in the set dose is determined by the processor arrangement based on the outputs from one or both of the sensor arrangements 136, 138. Following step S8, the operation returns to step S5.

If at step S6 the processor arrangement determines that both the first sensor arrangement is indicating a counter-clockwise movement of the dose setting component 113 and the second sensor arrangement is indicating a counter-clockwise rotation of the dose sleeve 114 within the body 101, the operation proceeds to step S9. This occurs because the processor arrangement has detected that a dose that is set or dialled into the medicament delivery device 100 is being decreased. At step S9, the value of the displayed dose is decreased. The decrease is made continuously such that the displayed dose value represents the dose that is set. The amount of the decrease in the set dose is determined by the processor arrangement based on the outputs from one or both of the sensor arrangements 136, 138. Following step S9, the operation returns to step S5.

If at step S7 the processor arrangement determines that both the first sensor arrangement is indicating a counter-clockwise movement of the dose setting component 113 and the second sensor arrangement is indicating no rotation of the dose sleeve 114 within the body 101, the operation proceeds to step S10. Here, the processor arrangement awaits the zero dose position to be reached. A positive determination from step S7 indicates that the set or dialled dose is being delivered. Once dose delivery has commenced, it cannot be stopped. As such, the processor arrangement is able to determine that the set dose will be delivered, although it requires detection of that at step S10.

Following step S10, the processor arrangement stores data indicative of the delivered dose at step S11. The delivered dose is stored in non-volatile memory. The delivered dose then is able to be communicated, displayed or otherwise used as required at a later time.

Various alternatives will be apparent to the skilled person and some such alternatives will now be described.

In the above, the second sensing arrangement 138, 148 detects rotation of the dose sleeve 114 by detecting movement of tick marks thereon. As such, the second sensing arrangement detects helical movement of the dose sleeve 114, although this appears as translational movement to the sensor 138. This sensing may be performed by a low resolution camera or a simpler photodetector arrangement. The second sensing arrangement 138, 148 may take any suitable form. For instance, it may include an optical sensor of the type often found in optical mice of the computer peripheral type. Alternatively, it may include an optical detector operating outside of the visible spectrum, for instance in infra red or ultraviolet. It may be other than an optical arrangement. It may be configured to detect pure axial movement of the dose sleeve 114, pure rotational movement, or helical movement (both rotational and axial).

Although a few embodiments have been shown and described, it would be appreciated by those skilled in the art that changes may be made in these embodiments without departing from the principles of the invention, the scope of which is defined in the claims.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively, or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoylgamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta-decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof

The invention claimed is:

1. A drug delivery device comprising:
   a housing;
   a dose sleeve located within the housing, the dose sleeve being configured to move helically within the housing as a medicament dose is dialled into or delivered from the drug delivery device;
   a dose setting arrangement coupled to the dose sleeve and configured to cause helical movement of the dose sleeve as a medicament dose is dialled into the drug delivery device through rotation of a dose dial member forming part of the dose setting arrangement;

a dose delivery arrangement comprising a dose button coupled to the dose sleeve and configured to cause delivery of medicament with helical movement of the dose sleeve and without rotation of the dose dial member when the dose button is actuated;

a first sensor configured for detecting a rotation of the dose dial member relative to the housing, the first sensor comprising two detectors configured to detect detectable features of the dose dial member as the detectable features pass by the two detectors during rotation of the dose dial member, wherein each of the two detectors provides an output signal;

a second sensor configured for detecting a helical movement of the dose sleeve relative to the housing, wherein the second sensor provides an output signal; and a processor coupled to receive the output signals of the first sensor and the output signal of the second sensor and the processor is configured to:
- calculate a rotation direction of the dose dial member from a phase of the respective output signals of the two detectors of the first sensor, and
- calculate a size of a medicament dose dispensed by the drug delivery device from the output signals of the first sensor and the output signals of the second sensor.

2. The drug delivery device according to claim 1, wherein the detectable features of the dose dial member comprise a first scale and the first sensor is arranged on a sliding member and is configured to detect the first scale.

3. The drug delivery device according to claim 1, wherein the first sensor is enabled to visually detect rotation of the dose dial member.

4. The drug delivery device according to claim 1, wherein the first sensor comprises optical transmitting and detecting transducers directed at the dose dial member.

5. The drug delivery device according to claim 2, wherein the first scale comprises an incremental encoder.

6. The drug delivery device according to claim 1, wherein the second sensor is configured to detect an axial movement of the dose sleeve relative to the housing.

7. The drug delivery device according to claim 1, wherein the second sensor is configured to detect a rotational movement of the dose sleeve relative to the housing.

8. The drug delivery device according to claim 1, wherein detectable features of the dose sleeve comprise a second scale and the second sensor is configured to detect the second scale,
wherein the second sensor and the second scale are subject to a relative displacement when the dose sleeve moves relative to the housing.

9. The drug delivery device as claimed in claim 8, wherein the second scale comprises tick marks.

10. The drug delivery device as claimed in claim 1, comprising a display configured to display a dialled dose.

11. The drug delivery device as claimed in claim 1, wherein the processor is configured to store data indicative of a delivered dose in non-volatile memory.

12. The drug delivery device according to claim 1, further comprising a cartridge which is at least partially filled with a medicament.

13. The drug delivery device according to claim 1, wherein each of the two detectors of the first sensor are electro-mechanical switches that are configured to engage with the detectable features of the dose dial member as the dose dial member is rotated.

14. The drug delivery device according to claim 1, wherein each of the two detectors of the first sensor are optodetectors that are configured to sense a presence of the detectable features of the dose dial member as the dose dial member is rotated.

15. The drug delivery device according to claim 1, wherein each of the two detectors of the first sensor are magnetic sensors that are configured to sense a magnetic field of the detectable features of the dose dial member as the dose dial member is rotated.

16. The drug delivery device according to claim 1, wherein the two detectors of the first sensor are located diametrically opposite of each other around the dose dial member and configured to sense a presence of the detectable features of the dose dial member as the dose dial member is rotated.

17. The drug delivery device according to claim 1, wherein the detectable features are located on an outside diameter of the dose dial member and comprise gnarls, protrusions, and/or ribs.

18. The drug delivery device according to claim 1, wherein the detectable features of the dose dial member comprise a plurality of protrusions located along an outer diameter of the dose dial member.

19. The drug delivery device according to claim 1, wherein the detectable features of the dose dial member each comprise a different magnetic property.

20. The drug delivery device according to claim 1, wherein the processor is configured to:
- determine when the dose dial member is not rotating based on the output signals of the first sensor;
- determine when the dose sleeve is rotating based on the output signal of the second sensor; and
- responsive to determining when the dose dial member is not rotating and the dose sleeve is rotating, storing a delivered dosage within a non-volatile memory of the drug delivery device.

* * * * *